United States Patent [19]
Wachtel et al.

[11] Patent Number: 6,060,501
[45] Date of Patent: *May 9, 2000

[54] COMBINED TREATMENT OF MULTIPLE SCLEROSIS

[75] Inventors: Helmut Wachtel, Berlin; Peter-Andreas Löschmann, Hechingen; Hermann Graf, Berlin, all of Germany; H. Daniel Perez, Kentfield, Calif.

[73] Assignee: Schering Aktiengesellschaft, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/937,081

[22] Filed: Sep. 24, 1997

Related U.S. Application Data

[63] Continuation of application No. 08/340,416, Nov. 15, 1994, abandoned, which is a continuation of application No. 08/253,938, Jun. 2, 1994, abandoned.

[51] Int. Cl.$^7$ .............................. A01N 43/76; A01N 43/36
[52] U.S. Cl. ............................................ 514/423; 514/376
[58] Field of Search ...................... 514/423, 376

[56] References Cited

U.S. PATENT DOCUMENTS

| | | | |
|---|---|---|---|
| 4,153,713 | 5/1979 | Huth et al. | 424/274 |
| 4,943,573 | 7/1990 | Meanwell et al. | 514/253 |
| 5,227,369 | 7/1993 | Rosen et al. | 514/23 |
| 5,420,154 | 5/1995 | Christensen, IV et al. | 514/424 |
| 5,541,219 | 7/1996 | Fenton et al. | 514/432 |

FOREIGN PATENT DOCUMENTS

| | | |
|---|---|---|
| 0 411 754 | 2/1991 | European Pat. Off. . |
| 92/02220 | 2/1992 | WIPO . |
| 92/19594 | 11/1992 | WIPO . |
| 93/16706 | 9/1993 | WIPO . |
| 93/19068 | 9/1993 | WIPO . |

OTHER PUBLICATIONS

"Differential modulation of tissue function and therapeutic potential of selective inhibitors of cyclic nucleotide phosphodiesterase isoenzymes", C.D. Nicholson et al., *TiPS*, vol. 12, Jan. 1991.

"Inhibition of Eosinophil Oxygen Radical Production by Type IV—But Not Type III—Selective cAMP Phosphodiesterase Inhibitors", G. Dent et al., *Br. J. Pharm.*, vol. 22 (163P), 1990.

"Pentoxifylline inhibits experimental allergic encephalomyelitis", S. Nataf et al., *Acta Neurol. Scand.*, vol. 88, 1993, pp. 97–99.

"Regulation of Tumor Necrosis Factor Expression in Macrophage–like Cell Line by Lipopolysaccharide and cyclic AMP", S.M. Taffet et al., *Cellular Immunology*, vol. 120, 1989, pp. 291–300.

"The identification of a new cyclic nucleotide phosphodiesterase activity in human and guinea–pig cardiac ventricle", M.L. Reeves et al., *Biochem J.*, vol. 241, 1987, pp. 535–541.

"Phosphodiesterase inhibitor pentoxifylline, a selective suppressor of T helper type 1– but not type 2–associated lymphokine production, prevents induction of experimental autoimmune encephalomyelitis in Lewis rats", O. Rott et al., *Eur. J. Immunol.*, vol. 23, 1993, pp. 1745–1751.

"The specific type III and IV phosphodiesterase inhibitor zardaverine suppresses formation of tumor necrosis factor by macrophages", F.U. Schade and C. Schudt, *Eur. J. Pharma.*, vol. 230, 1993, pp. 9–14.

"Multiple Sclerosis and Allied Demyelinative Diseases", *Principles of Neurology*, 1993, pp. 777–791.

Abstract, "Tumor–necrosis factor–directed therapy of autoimmune . . . ", Sommer et al., *J. Neurol.* vol. 54(1–2), 1994, p. 198.

Spengler et al., "Dynamics of Cyclic AMP– and Prostaglandin . . . ," *Infection and Immunity*, 57(9):2837–2841, Sep. 1989.

Lloyd J. Old, "Tumor necrosis factor: Another chapter in the long . . . ," *Nature*, vol. 330, pp. 602–603, Dec. 17, 1987.

Millar et al., "Tumour Necrosis Factor in Bronchopulmonary . . . ," *Lancet*, vol. II for 1989, pp. 712–714, Sep. 23, 1989.

Dezube et al., "Pentoxifylline and wellbeing in patients with cancer," *Lancet*, 335(8690):662, Mar. 17, 1990.

Frölich et al., "Is the Elevation of Cyclic . . . ," *J. Invest. Dermat.*, 90(2):240, 1988.

Marivet et al., "Inhibition of Cyclic Adenosine–3',5'–monophosphate . . . ," *J. Med. Chem.*, 32:1450–1457, 1989.

"Pentoxifylline inhibits experimental allergic encephalomyelitis", S. Nataf et al., *Acta Neurol. Scand.*, vol. 88, 1993, pp. 97–99.

"Differential regulation of TNF–$\alpha$ and IL–1$\beta$ production from endotoxin stimulated . . . ", Molnar–Kimber et al., *Mediators of Inflammation*.

Sharief et al., "Association Between Tumor Necrosis Factor–alpha . . . ," *New England J. of Med.*, 325(7) :467–472, Aug. 15, 1991.

Kirby et al., "Prostacyclin Increases Cyclic–Nucleotide . . . ," *The Lancet*, 2(8192):453–454, Aug. 30, 1980.

Renz et al., "Release of Tumor Necrosis Factor–$\alpha$ From Macrophages . . . ," *J. of Immunology*, pp. 2388–2393, Oct. 1, 1988.

Strieter et al., "Cellular and Molecular Regulation of Tumor . . . ," *Biochem. and Biophys. Research Comm.*, 155(3):1230–1236, Sep. 30, 1988.

"Demyelinating Diseases", *Cecil Textbook of Medicine*, Wyngaarden et al., eds., 19th ed., 1992, pp. 2199–2200.

Lowe et al, *J. Med. Chm* 1991 vol. 34, p624–28.

Merch Manual, 14$^{th}$ ed, 1982, p 1354–56.

*Primary Examiner*—Russell Travers
*Attorney, Agent, or Firm*—Millen, White, Zelano, & Branigan, P.C.

[57] ABSTRACT

A pharmaceutically composition for treating MS comprising an effective amount of a combination of a PDE IV inhibitor and an anti-inflammatory and immunomodulatory drug in a pharmaceutically acceptable carrier.

18 Claims, No Drawings

COMBINED TREATMENT OF MULTIPLE SCLEROSIS

This application is a continuation of application Ser. No. 08/340,416, filed Nov. 15, 1994, now abandoned, which is a continuation of application Ser. No. 08/253,938, filed Jun. 2, 1994 now abandoned.

Multiple sclerosis (MS) is a severe chronic disabling disease with characteristic demyelination in the CNS triggered by probable autoimmune mechanisms in a genetically susceptible population. An environmental factor which most often acts in childhood activates a specific population of T-cells (with the potential of attacking myelin-associated antigens such as MBP, MAP, MOP or others) which normally is controlled by suppressor-cells. In many MS cases, non-specific stress results in disease exacerbations with opening of the BBB, edema, immigration and activation of T-cells and macrophages and subsequent destruction of oligodendroglia-associated myelin followed by failing attempts at remyelination and finally a glia scar (relapsing-remitting form of MS). These exacerbations which can be visualised by MRI are associated, depending on location, with severe functional disabilities; furthermore, with an increasing number of relapses the disease (and the antigens being attacked) becomes more generalised and progresses with less clearcut intervals (progressive form of MS, secondary or primary) and increasing and persisting disability which causes (in this mostly young population) impairment of life quality with loss of employment and independent life (with hospitalisation and eventually death). Classic non-specific immunosuppressive therapies (including corticosteroids) and cytostatic drugs as a rule have failed to alter this sequence of events and disease progression—possibly because they are poorly tolerated in these patients and also because they inhibit endogenous immunosuppressive mechanisms as well. Recently non-specific immunomodulatory therapy with interferon-$\beta$-1b has been shown to prolong disease-free intervals in patients with beginning relapsing/remitting MS; however, in the great majority of these patients, exacerbations cannot be prevented completely, and also the effect on disability during the first three years of therapy is still small. Corticosteroid therapy relieves some acute symptoms of these exacerbations (probably by reducing edema) but does not affect longterm prognoses. However, it appears of utmost importance to suppress all exacerbations with their activation, extension and amplification of autoimmune mechanisms which make the disease uncontrollable and disabling. Indeed recent advances in the clinical, biochemical and imaging technologies enable clinicians to predict and diagnose such exacerbations in a very early stage, and thus, it now becomes possible to combine different therapeutic strategies to achieve a maximal therapeutic effect. Immunomodulatory therapies with non-specific mechanisms, e.g. with interferon-$\beta$-1b (or specific immunomodulatory drugs such as copolymer I, if proven to be effective, as well as recent attempts to induce tolerance to MS antigens) which will never work to 100% as they need to be given before the onset of the disease, but they can reduce to a clear and significant degree the number of clinical exacerbations and, even more, of lesions in the brain. Fortunately for the target of bringing disease activity to a complete hold, the new diagnostic techniques being developed have the potential to detect the very early beginning of an exacerbation (e.g. increases in $\gamma$-interferons, TNF-$\alpha$, increased number of activated specific T-cells in the blood, new specific MRI and other imaging techniques, and clinical observation).

Therefore, strong and efficient drugs are necessary which act not just on some symptoms of the exacerbation but are able to prevent them completely and thus, inhibit disease progression. However, also new therapeutic strategies which aim e.g. at peripheral T-cell activation, endothelial adhesion, opening of blood-brain barrier and activation of the T-cell-macrophage/microglia interaction with subsequent oligodendrocyte damage and demyelination do affect defense mechanisms not just in the autoimmune condition but, on chronic use, are also damaging vital defense mechanism against exogenous (e.g. bacterial, parasitic or viral infections) as well as against endogenous noxes (e.g. tumorigenesis). The new concept of this invention is, however, to combine well tolerated chronic maintenance therapy with the use of new diagnostic techniques to predict or detect early exacerbations which can then, but only then, be treated aggressively by a number of new drugs (or their combinations) in order to ensure that no persistent CNS lesions can be produced with their fatal influence on disease exacerbation, extension and progression. Furthermore, combination of therapies with different mechanisms to achieve maximum efficacy will improve tolerability of therapy (as the effects of interferon-$\beta$-1b in MS have been shown to be dose-dependent, higher dosages could be expected to achieve higher and even 100% efficacy, but increasingly severe side effects prevent this type of treatment), and finally, these new combinations of maintenance and anti-exacerbation therapies result in a clearly reduced risk of side effects which can be caused by high-dose and long-term use of these drugs in monotherapy. Indeed when basic maintenance therapy is being combined with the use of these new strategies only when needed (e.g. during or just before an exacerbation) less side effects of both complementary and synergistic therapeutic lines do occur and these forms of therapy can be combined to achieve an optimal clinical result. Also in this new concept of short-term therapy of exacerbations, different drugs can be combined to prevent further damage and disease progression. Thus inhibition of synthesis of cytotoxic cyto- and chemokines can be combined with drugs which inhibit their release, and both may be enhanced in efficacy by, e.g., simultaneous inhibition of traffic across the blood-brain barrier, or with other drugs which inhibit—or even reverse—the ultimate tissue damage (e.g., nerve growth factors, calcipotriols, calpain inhibitors etc.).

By "immunomodulatory drugs", it is meant, e.g., agents which act on the immune system, directly or indirectly, e.g., by stimulating or suppressing a cellular activity of a cell in the immune system, e.g., T-cells, B-cells, macrophages, or other APC cells, or by acting upon components outside the immune system which, in turn, stimulate, suppress, or modulate the immune system, e.g., hormones, receptor agonists or antagonists, and neurotransmitters; immunomodulators can be, e.g., immunosuppressants or immunostimulants.

By "anti-inflammatory drugs", it is meant, e.g., agents which treat inflammatory responses, i.e., a tissue reaction to injury, e.g., agents which treat the immune, vascular, or lymphatic systems.

Again, in this new combined therapeutic strategy, there are also many steps where the presumed cascade of MS can be attacked by existing or future drugs (see simplified schedule) after the initial specific or non-specific causes, which include impairment of suppressor T-cell effects on myelin-specific autoimmune T-cells:

| pathogenic cascade | possible therapeutic intervention |
|---|---|
| 1. activation of peripheral specific T-cells which are potentially autoreactive to myelin | destroy these T-cells, reactivate tolerance by oral antigens, immune globulins? enhance suppressor mechanisms, e.g. by interferon β-1b |
| 2. enhanced blood-brain barrier permeability to these T-cells | close blood-brain barrier, e.g. by anti-adhesion molecules such as anti-integrin monoclonal antibodies? |
| 3. immigration of macrophages, and macrophage - T-cell - interaction and activation | interfere with T-cell receptors, enhance suppressor mechanisms, e.g. by interferon β-1b |
| 4. local inflammation and edema | non-specific anti-inflammatory and anti-edema strategies, e.g. corticosteroids |
| 5. enhanced local release of γ-interferons, TNFα and other cytotoxic cytokines | antagonize γ-interferon, TNFα and other cytotoxic cytokines by acting on synthesis, release or other targets (e.g. receptors), e.g. by interferon β-1b |
| 6. oligodendrocyte injury with acute myelin breakdown and degradation of axonal lamellae by microglia/macrophages | prevent myelin injury, e.g. with external competing antigens, such as CoP I? |
| 7. acute conduction block, with functional impairment | act on ion channels, e.g. potassium channel blockers? |
| 8. chronic de- and re-myelination process, functional adaptation and reorganisation within the brain | enhance oligodendrocyte remyelination mechanisms, e.g. by glial growth factors? or Schwann cell implantation? |
| 9. persisting lesion without or with astrocyte scare and functional impairment, depending on size and location | symptomatic therapies against spasticity, fatigue, urinary problems etc., therapeutic aids and training of remaining skills |

Whilst many compounds can attack one or another of these MS mechanisms and have, as a rule, typical risks and side effects associated with any specific mechanism, our experimental studies have, surprisingly, demonstrated that inhibitors of phosphodiesterase IV such as rolipram, by acting in a selective way on postreceptorial intracellular signalling mechanisms of the cAMP-metabolism do not affect just one mechanisms but combine, by their very basic way of acting, a number of useful biochemical and pharmacological effects which in their sum make these drugs in combinations superior to other strategies:

cAMP PDE IV inhibitors do stabilize the blood-brain barrier respectively restore stability vs. humoral and cellular factors from the blood (including cytokines, interferons, antibodies, T-cells, mononuclear cells, plasma cells and granulocytes)

exert a general anti-inflammatory effect by inhibiting activation and interactions between different cellular and humoral elements mediating inflammation suppress the release of cytotoxic mediators from immune, endothelial and glial cells (e.g. TNF's γ-interferons and other cytokines)

inhibit migration and chemotaxis of cells of the immune system inhibit proliferation of microglia and astrocytes and thus reduce local inflammation and scar formation suppress the release or synthesis of reactive oxygen radicals from immune cells or damaged parenchema cells etc.

By combining all these effects specific phosphodiesterase inhibitors have greatest therapeutic potential and indeed are very highly effective on human MS cells as well as in different animal models of the disease (e.g. EAE, EAN in different species); furthermore in different human conditions, their safety and efficacy on different biological parameters has already been observed. With these combined mechanisms it is obvious that low dosages can be used which in monotherapy or even more so in combination with other maintenance therapies can be used to prevent relapses or reduce or treat exacerbations of MS with very minor side effects (in contrast to other therapies).

Furthermore, at the same or lower (exceptionally also higher) dosages these drugs can be combined with the other compounds as described from 1–9 to achieve additive and synergistic therapeutic effects in order to achieve maximum efficacy (and thus inhibition of progression as described previously) with an minimum of side effects.

The present invention relates to a method of treating or preventing MS comprising administering an effective amount of a combination of a Type IV phosphodiesterase inhibitor (PDE IV inhibitor) and antiinflammatory or immunomodulatory drugs.

The phosphodiesterase PDE inhibitors suitable for use in this invention are preferably cycloadenosine-3',5'-monophosphate (cAMP) PDE type IV (PDE IV) inhibitors according to the modern classification (J. A. Beavo and D. A. Reifsnyder, Trends Pharmacol. Sci. 11; 150–155, 1990) and include but are not limited to compounds disclosed in U.S. Pat. No. 4,193,629, WO 92/02220; U.S. Pat. No. 4,186,129; BP 247 725; U.S. Pat. No. 5,064,854; N. A. Saccamono et al., J. Med. Chem. 34: 291–298, 1991; F. J. Vinick et al., J. Med. Chem. 34: 86–89, 1991; J. A. Lowe et al., J. Med. Chem. 34: 624–628, 1991;

1,3-dibutyl-3,7-dihydro-7-(2-oxopropyl)-1H-purin-2,6-dione (denbufylline, BRL 30892);

4-[(3-butoxy-4-methoxyphenyl)methyl]-2-imidazolidinone (RO 20-1724);

5,6-diethoxybenzo[b]thiophen-2-carboxylic acid (tibenelast, LY 186655);

3-ethyl-1-(3-nitrophenyl)-2,4 (1H, 3H)-chinazolinedione (nitraquazone, TVX 2706);

6-(3,6-dihydro-6-methyl-2-oxo-2H-1,3,4-thiadiazine-5-yl)-1-(3,4-dimethoxybenzoyl)-1,2,3,4-tetrahydro-4,4-dimethylchinoline (EMD 54622);

1-ethyl-4-[(1-methylethyliden)hydrazino]-1H-pyrazolo[3,4-b]pyridin-5-carboxylic acid ethylester (etazolate);

N-hydroxy-5,6-dimethoxy-benzo[b]thiophene-2-carboximidamid (Org 30029);

2-amino-6-methyl-4-propyl-(1,2,4)triazolo[1,5-a]pyrimidine-5(4H)-one (ICI 63197);

6-[4-(difluoromethoxy)-3-methoxyphenyl]-3(2H)-pyridazinone (zardaverine) pentoxifilline; propentofilline; vinpocetine and the pharmaceutically acceptable salts thereof.

Preferred PDE IV inhibitors are racemic and optically active compounds of formula I

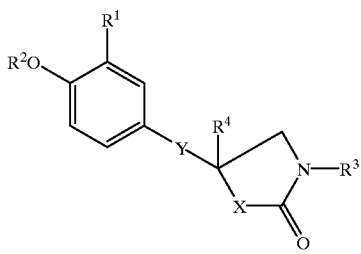

(I)

wherein
$R^1$ is $C_{1-6}$-alkyl, a heterocyclic ring, or $OR^5$; and
$R^5$ is $C_{1-6}$-alkyl, $C_{3-7}$-cycloalkyl, $C_{2-6}$-alkenyl, $C_{3-7}$-alkinyl, $C_{3-7}$-cycloalkyl-$C_{1-2}$-alkyl, aryl, aralkyl, a heterocyclic ring or $C_{1-6}$-alkyl substituted by one or more halogen atoms, hydroxy, carboxy, $C_{1-4}$-alkoxy, $C_{1-4}$-alkoxycarbonyl, or an optionally alkyl substituted amino group;
$R^2$ is $C_{1-4}$-alkyl, $C_{2-4}$-alkenyl, or $C_{2-4}$-alkinyl;
$R^3$ is a hydrogen atom, $C_{1-6}$-alkyl, aryl, aralkyl, or aryl optionally substituted by one or two methyl groups or $C_{1-6}$-alkanoyl;
$R^4$ is a hydrogen atom or $C_{1-6}$-alkyl;
Y is a direct bond or a $CH_2$ group;
X is $CH_2$, $CH_2$—$CH_2$, NH, or an oxygen atom and the pharmaceutically acceptable salts thereof.
Preferred compounds of formula I are those wherein
$R^2$ is methyl;
$R^3$ is a hydrogen atom or $C_{1-6}$-alkanoyl;
$R^1$ is $OR^5$; $R^5$ is $C_{1-6}$-alkyl, $C_{3-7}$-cycloalkyl, or 3-tetrahydrofuranyl;
$R^4$ is hydrogen or $C_{1-4}$-alkyl; and
X is a $CH_2$ group or oxygen.

More preferred compounds of formula I are those wherein $R^3$ is hydrogen.

Specifically exemplified are 4-(3-cyclopentyloxy)-4-methoxyphenyl)-2-pyrrolidinone (rolipram) and 5-methyl-5-(3-cyclopentyloxy-4-methoxyphenyl)-2-oxazolidinone.

The term "alkyl" as used herein include straight or branched alkyl radicals, for example methyl, ethyl, n-propyl, isopropyl, n-butyl, sec.-butyl, isobutyl, tert.-butyl, pentyl, 2-methyl-butyl, 2,2-dimethylpropyl and hexyl.

By the term "alkenyl" as used herein is meant to include, but not limited to vinyl, 1-propenyl, 2-propenyl, 2-propinyl or 3-methyl-2-propenyl.

By the term "cycloalkyl" or "cycloalkyl alkyl" as used herein is meant to include groups of 3–7 carbon atoms, such as cyclopropyl, cyclopropylmethyl, cyclopentyl or cyclohexyl. By the term "aryl" or "aralkyl" as used herein is meant an aromatic ring or ring system of 6–10 carbon atoms, preferably monocycle, such as phenyl, benzyl, phenethyl or naphthyl.

By the term "heterocyclic ring" as used herein is meant a saturated ring of 5 to 6 members having a single oxygen, sulfur or nitrogen atom, such as, but not limited to 2- and 3-tetrahydropyranyl, 2- and 3-tetrahydrofuranyl, pyrrolidino, 2- and 3-pyrrolidyl, piperidinino, 2-, 3- and 4 piperidyl and the corresponding N-alkyl pyrrolidyl and piperidyl rings wherein the alkyl is of 1–4 carbon atoms. Also encompassed within the scope of this invention are heterocyclic rings having more than one hetero atom such as morpholino, piperazino or N-alkyl piperazino.

By the term "halo" as used herein is meant all halogens, i.e., chloro, fluoro, bromo and iodo.

The preparation of the compounds of formula I can be carried out by the procedure outlined in the above-mentioned patents or by U.S. Pat. Nos. 4,153,713; 4,186,129; and 5,298,628; WO 86/02268; or EP 0 247 725. Rolipram is 4-[(3-cyclopentyloxy)-4-methoxyphenyl]-2-pyrrolidinone. See, e.g., Merck Index, 11th edition, pp. 1312–1313. Rolipram and related compounds can be prepared, e.g., according to U.S. Pat. No. 4,193,926. The antiinflammatory and immunomodulatory drugs suitable for use in this invention include but are not limited 1. interferone derivatives, e.g., betaserone, β-interferone
2. prostane derivatives, e.g., compounds disclosed in PCT/DE93/0013, e.g., iloprost, cicaprost
3. glucocorticoid, e.g., cortisol, prednisolone, methylprednisolone, dexamethasone
4. immunsuppressives, e.g., cyclosporine A, FK-506, methoxsalene, thalidomide, sulfasalazine, azathioprine, methotrexate
5. lipoxygenase inhibitors, e.g., zileutone, MK-886, WY-50295, SC-45662, SC-41661A, BI-L-357
6. leukotriene antagonists, e.g., compounds disclosed in DE 40091171 German patent application P 42 42 390.2; WO 9201675; SC-41930; SC-50605; SC-51146; LY 255283 (D. K. Herron et al., FASEB J. 2: Abstr. 4729, 1988); LY 223982 (D. M. Gapinski et al. J. Med. Chem. 33: 2798–2813, 1990); U-75302 and analogs, e.g., described by J. Morris et al., Tetrahedron Lett. 29: 143–146, 1988, C. E. Burgos et al., Tetrahedron Lett. 30: 5081–5084, 1989; B. M. Taylor et al., Prostaglandins 42: 211–224, 1991; compounds disclosed in U.S. Pat. No. 5,019,573; ONO-LB-457 and analogs, e.g., described by K. Kishikawa et al., Adv. Prostagl. Thombox. Leukotriene Res. 21: 407–410, 1990; M. Konno et al., Adv. Prostagl. Thrombox. Leukotriene Res. 21: 411–414, 1990; WF-11605 and analogs, e.g., disclosed in U.S. Pat. No. 4,963,583; compounds disclosed in WO 9118601, WO 9118879; WO 9118880, WO 9118883,
7. antiinflammatory substances, e.g., NPC 16570, NPC 17923 described by L. Noronha-Blab. et al., Gastroenterology 102 (Suppl.): A 672, 1992; NPC 15669 and analogs described by R. M. Burch et al., Proc. Nat. Acad. Sci. USA 88: 355–359, 1991; S. Pou et al., Biochem. Pharmacol. 45: 2123–2127, 1993;
8. peptide derivatives, e.g., ACTH and analogs; soluble TNF-receptors; TNF-antibodies; soluble receptors of interleukines, other cytokines, T-cell-proteins; antibodies against receptors of interleukines, other cytokines, T-cell-proteins.
9. calcipotriols and their analogues as activators of syntheses of different nerve growth factors, or these growth factors themselves or small peptides thereof which stimulate oligodendrocyte growth (or prevent their apoptosis or destruction) and enhance remyelination.

Our data show that in their effects on human MS calls as well as in different animal models of demyelinating disease (e.g. different EAE models) various of these new drugs can be combined successfully to achieve better protection with less side effects.

The present invention generally relates to the treatment of MS with a combination of a PDE IV inhibitor with an interferon derivative, a prostane derivative, a glucocorticoid, an immunsuppressant, a lipoxygenase inhibitor, a leukotriene antagonist, an antiinflammatory substance, a peptide derivative or a calcipotriol or analog thereof.

A prefered combination consists a PDE IV inhibitor and an interferon derivative, a prostane derivate or a leukotriene antagonist e.g. betaserone, iloprost, cicaprost or 5-[(E)-(2S)-

2-((1E,3E)-5S)-5-hydroxy-6,6-trimethylene-9-phenyl-1,3-nonadiene-8-inyl)-cyclohexylidene]-pentanoic acid or esters thereof.

The present invention also relates to the use of combination for preventing, and/or ameliorating disease severity, disease symptoms, and/or periodicity of recurrence of the disease, e.g., lengthening the time period between episodes in which symptoms flare, and/or suppressing the ongoing immune or autoimmune response associated with the disease (which untreated enhances disease progression and disability).

The invention thus relates to the administration of an effective amount of such a combination to a patient to prevent or treat MS. The amount of said compounds administered is an amount which is effective, for example, in preventing or ameliorating the symptoms of the disease or the disease's recurrence, or affecting the ultimate course of the disease, e.g., blocking disease activation, cell trafficing across the blood-brain barrier, the inflammatory response in the brain, the appearance of inflammatory lesions, neuronal or neuroglia cell death, and/or demylination and the symptoms typically associated with pathogenesis of the disease.

The present invention also provides pharmaceutical compositions comprising an effective amount of a combination of a Type IV phosphodiesterase inhibitor and an above mentioned drug in a pharmaceutically acceptable carrier.

Since the present invention relates to a method of treatment comprising a combination of such active agents wherein the active agents may be administered separately, the invention relates to combining separate pharmaceutical compositions in kit form.

According to the present invention, a pharmaceutical composition comprising an effective amount of a combination described above can be administered to patients having multiple sclerosis, e.g., multiple sclerosis variants such as Neuromyelitis Optica (Decic's Disease), Diffuse Sclerosis, Transitional Sclerosis, Acute Disseminated Encephalomyelitis, and Optic Neuritis, but also Guillain-Barre's Syndrom, virus-, bacteria- or parasite-related demylinating or otherwise degenerative brain disease such as encphalopathies related to HIV, meningococcal or toxoplasma infections, central malaria, Lyme's disease etc. Symptoms of MS which are prevented or ameliorated or treated include: weakness and/or numbness in one or more limbs; tingling of the extremities and tight band-like sensations around the trunk or limbs; dragging or poor control of one or both legs to spastic or ataxic paraparesis; hyperactive tendon reflexes; disappearance of abdominal reflexes; Lhermitte's sign; retrobulbar or optic neuritis; unsteadiness in walking; increased muscle fatiguability; brain stem symptoms (diplopia, vertigo, vomiting); disorders of micturition; hemiplegia; trigeminal neuralgia; other pain syndromes; nystagmus and ataxia; cerebellar-type ataxia; Charcot's triad; diplopia; bilateral internuclear ophthalmoplegia; myokymia or paralysis of facial muscles; deafness; tinnitus; unformed auditory hallucinations (because of involvement cochlear connections); vertigo and vomiting (vestibular connections); transient facial anesthesia or of trigeminal neuralgia; bladder dysfunction euphoria; depression; fatigue; dementia, dull, aching pain in the low back; sharp, burning, poorly localized pains in a limb or both legs and girdle pains; abrupt attacks of neurologic deficit; dysarthria and ataxia; paroxysmal pain and dysesthesia in a limb; flashing lights; paroxysmal itching; and/or tonic seizures, taking the form of flexion (dystonic) spasm of the hand, wrist, and elbow with extension of the lower limb. A patient having MS may have one or more of these associated with MS and one or more can be ameliorated by administrating of a combination according to the present invention.

The administration of the combination can also block or reduce the physiological and pathogenic deterioration associated with MS, e.g., inflammatory response in the brain and other regions of the nervous system, breakdown or disruption of the blood-brain barrier, appearance of lesions in the brain, tissue destruction, demyelination, autoimmune inflammatory response, acute or chronic inflammatory response, neuronal death, and/or neuroglia death. The combination is useful to treat the different types of MS, including the multifocal, CNS, relapsing and remitting course; the multifocal, CNS, progressive course; the single-site, relapsing and remitting course; and other variants of multiple sclerosis. See, e.g., *Cecil's Textbook of Medicine*, edited by James B. Wyngaarden, 1988. Effects of the administration of the combination include, e.g., preventing the disease, ameliorating symptoms of the disease, reducing the annual exacerbation rate (i.e., reducing the number of episodes per year), slowing the progression of the disease, or reducing the appearance of brain lesions (e.g., as identified by MRI scan) and postponing or preventing disability, loss of employment, hospitalisation and finally death. The episodic recurrence of the mentioned diseases such as MS can be ameliorated, e.g., by decreasing the severity of the symptoms (such as the symptoms described above) associated with the, e.g., MS episode, or by lengthning the time period between teh occurrence of episodes, e.g., by days, weeks, months, or years, where the episodes can be characterized by the flare-up and exacerbation of disease symptoms, or preventing or slowing the appearance of brain inflammatory lesions. See, e.g., Adams, R. D., Principles of Neurology, 1993, page 777, for a description of a neurological inflammatory lesion.

By "Type IV phosphodiesterase inhibitor", "specific Type IV phosphodiesterase inhibitor", and similar expressions are meant a selective i.e., specific, such inhibitor, where the compound binds to or inhibits preferentially the Type IV phosphodiesterase when compared to known types of phosphodiesterase types, e.g., I, II, or III, e.g., whereby the compound has a lower $IC_{50}$ (more potent) for the Type IV phosphodiesterase, such as where the $IC_{50}$ is, e.g., 2-fold, 5-fold, 10-fold, 50-fold, or more potent, for the Type IV phosphodiesterase compared to another known type of phosphodiesterase, e.g., I, II, or III. Such selectivity of a compound according to the present invention for a Type IV phosphodiesterase can also be conferred by other means, such as the manner in which it is delivered to its target, e.g., the compound can be associated with an agent which targets it to a specific tissue or cell type having the Type IV phosphodiesterase; the manner in which it interacts with the host's metabolism and/or physiology; or synthesizing PDE inhibitor prodrugs where activation of the PDE inhibitor is accomplished by enzymes present in the desired cells or tissues but absent in others.

The specific inhibition of a Type IV phosphodiesterase can be measured conventionally, e.g., according to the methods described in Reeves et a., *Biochem. J.* 241:535–541, 1977; by macrophage assay, as described, e.g., in Schade et al., *Europ. J. Pharmacol.*, 230:9–14, 1993; or WO 93/19068. For a review of phosphodiesterase specificity and how to determine it, see, e.g., Nicholson et al., *Trends Pharmacol. Sci.*, 12:19–27 (1991).

The activity of this invention of Type IV phosphodiesterase inhibitors such as Rolipram can be detected, for example, in animals suffering from Experimental allergic Encephalyelitis (EAE), an experimental T-lymphocyte initiated disease of the CNS. It can be produced, e.g., in rodents, guinea pigs, rabbits, and primates, by, e.g., immunizing animals with myelin, e.g., from a human brain, and/or corticosteroid administration over a long period of time. It can also be produced by injecting an animal with T-lumphocytes obtained from an animal suffering from EAE.

In particular, the activity can be detected in *Callithrix jacchus* (common marmoset) which has been immunized with myelin, e.g., from a human brain. The *Callithrix jacchus* develops EAE with essentially similar histophathology and neurological symptoms as those at certain stages of the human disease, MS, and has the further advantage that the development and course of the disease can be evaluated easily by MRI—where rolipram and related compounds by their unique and new spectrum of activity alone and in combinations as described have been shown to be effective at very low dosages and without interfering with CNS or other normal functions.

The components of the combination can be administered in the same pharmaceutical composition or by co-administration of separate pharmaceutical compositions.

The pharmaceutical compositions according to the present invention are prepared conventionally, comprising substanecs which are customarily used in pharmaceuticals, e.g., *Remington's Pharmaceutical Sciences*, 18th ed., Mack Publishing Company (1990), including excipients, carriers, adjuvants and buffers. The compositions can be administered, e.g., parenterally, enterally, orally, intramuscularly, topically, subcutaneously, intravenously, by aerosol, intrathecally directly into the cerebral spinal fluid of the CNS, or preferably by sustained release using, e.g., an implanted mini-osmotic pump (e.g., the ALZET pump manufactured by ALZA Corporation, P. O. Box 10950, Palo Alto, Calif., 94303), or other routes useful to achieve an effect.

Conventional excipients include pharmaceutically acceptable organic or inorganic carrier substances suitable for parenteral, enteral or topical application which do not deleteriously react with the agents. Suitable pharmaceutically acceptable adjuvants include, but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, cyclodextrins, etc. The pharmaceutical preparations can be sterilized, and if desired, mixed with stabilizers, wetting agents, emulsifiers, salts for influencing osmotic pressure, buffers, coloring, flavoring and/or aromatic substances, etc., which do not react deleteriously with the active compounds.

For parenteral application, particularly suitable are injectable sterile solutions, preferably oil or aqueous solutions, as well as suspensions, emulsions or implants, including suppositories. Ampoules are convenient unit dosages.

For enteral application, particularly suitable are tablets, dragees, suppositories or capsules having talc and/or a carbohydrate carrier or binder. The carrier may be lactose, corn starch, potato starch or a combination thereof. A syrup or elixir may be used when a sweetened vehicle is employed.

The compositions can also be formulated in an aqueous solution, optionally with the addition of additives customary in galenicals, for example, buffers; electrolytes such as sodium chloride; antioxidants such as ascorbic acid; adjuvants, e.g., methyl cellulose, lactose and mannitol and/or surfactants, e.g., lecithins and Tweens and/or aromatic substances for flavoring, e.g., ethereal oils.

Amounts of other Type IV phosphodiesterase inhibitors and combinations thereof can be determined routinely based on the information given herein, e.g., using the EAE model. However, any amount which is effective in treating MS can be administered to ameliorate or treat the disease. Dosages are determined conventionally, see, e.g., *Remington's Pharmaceutical Sciences*, 18th ed., Mack Publishing Company (1990). The composition may be administered in a single dose unit or in multiple dosages administered, e.g., twice, three, or four times a day, or by an osmotic pump, which delivers the drug(s) continuously. A Type IV phosphodiesterase inhibitor can be administered at the same time as the anti-inflammatory or immunomodulatory drug in a single or separate dosage unit, or a Type IV phosphodiesterase inhibitor can be administered at a different time from the anti-inflammatory or immunomodulatory drug, e.g., sequentially.

The exact dose of any component or combination to be administered is determined by the attending clinician and is dependent, e.g., on the potency of the compound administered, the age, weight, condition, and response of the patient.

The PDE IV inhibitor is administered alone in amounts of about 0.005 to about 0.1 mg/kg/day, and the immunomodulatory or anti-inflammatory is administered alone in amounts of, e.g., about 0.01 $\mu$g/kg/day for a prostacyclin or to about 10 mg/kg/day for a steroid. According to the present invention, the latter can be administered in lower doses than would be expected for purely additive effects, e.g., about 0.0005 to about 0.01 mg/kg/day for a PDE IV inhibitor and about 0.001 $\mu$g/kg/day to about 1 mg/kg/day for an immunomodulatory or anti-inflammatory drug.

Since the present invention relates to treatment of MS with a combination of active ingredients wherein said ingredients can be administered separately, the invention also relates to combining separate pharmaceutical compositions in kit form. The kit form is particularly advantageous when the separate components are administered in different dosage forms (i.e., oral and parenteral) or are administered at different dosage intervals.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents, and publications cited herein are hereby incorporated by reference.

EXAMPLES

To assess the ability of rolipram alone or in various combination as described to modify autoimmune processes, we investigated its influence on TNF production in vitro by MBP-specific T cell lines from MS patients and Lewis rats. MBP is a major candidate antigen in MS, and T cell-mediated immunity is of crucial importance in its pathogenesis. Similar to EAE, MBP-specific T cells in humans are often cytotoxic, of Th1 type secreting interferon (IFN)-gamma and TNF/LT, and recognize epitopes that are also encephalitogenic in EAE.

Rolipram selectively inhibited TNF production by human MBP-specific T cell lines (TCL) in a dose-dependent manner alone and in combination.

Similar results were found using an encephalitocenic CD4+MBP-specific rat TCL (L1402). TNF/LT (lymphotoxin) production measured in a cytotoxicity bioassay (18) was inhibited in a dose range comparable to the human lines (FIG. 1b). Moreover, inhibition was stereospecific with the (−)-enantiomer being 55 times more effective than the (+)-enantiomer. The $EC_{50}$ of (−)-rolipram, (+)-rolipram, and (−)-rolipram given alone were 20 nM, 280 nM, and 1100 nM, respectively. Previous investigations had shown that inhibition of cAMP PDE by rolipram is stereospecific. In vitro and in vivo binding data in mouse and rat forebrain tissue with $^3$H-rolipram proved for the (−)-enantiomers a 15–30 times higher affinity than the (+)-enantiomers (19). In line with these findings, our data strongly suggest that rolipram inhibits TNF/LT production in human and rat autoreactive T cells by an intracellular cAMP PDE dependent mechanism.

TNF and LT may both be produced by autoactive T cells. CD4+ cells have been reported to be the major source of TFN in autoimmune insulitis of NOD mice. The cytokine bioassay for TNF/LT detection employed here is sensitive to TNF and LT, but is 200 times more sensitive to the former.

The results of our in vivo findings prompted us to perform treatment experiments in EAE after active immunization (aEAE) and adoptive cell transfer (tEAE) in Lewis rats (21). When rolipram was administered from day 7 through day 23 in aEAE as monotherapy or in various combinations, the appearance of neurological symptoms was completely prevented. In clinically manifest EAE, treatment was started within 6 hours of the onset of symptoms. In the treated group disease did only progress moderately, whereas the controls developed severe EAE. None of the rolipram-treated animals developed grade 4 (paraplagia), whereas 4 to 7 animals in the vehicle-treated control group reached this level of impairment in one typical experiment. In tEAE similar effects were observed (21). Prophylactic treatment resulted in only minor symptoms with a mean maximum score (MMN) of 0.3±0.11 (n=5) in the treated group, as compared to 2.5±0.25 (n=5) in the controls (p<0.01). Treatment after onset of symptoms also lead to a marked reduction in maximum severity (treated group: MMS 0.7±0.10, n=5; vehicle treated matched controls 2.45±0.56, n=5, p<0.01).

In order to distinguish further between a long-term prophylactic or a temporary suppressive effect, animals received the drug from the day of active immunisation until day 11. With this regimen aEAE in treated animals was delayed by 3.5 days, but disease severity and duration was otherwise similar compared to the controls. This indicates that suppression of EAE and presently TNF/LT production is temporary, and deletion of autoreactive T cells by rolipram, as e.g., in the case of cyclophosphamide, is therefore unlikely.

Histological analysis was performed on selected animals with aEAE. There were only few and mild cellular lesions in the prophylactically treated animals. By contrast, two of three animals that were treated after onset of clinical signs showed cellular infiltrates similar to those in the controls. Previous investigations have shown that inflammatory infiltrates in the central nervous system do not necessarily correlate with the degree of neurological deficit. In a study on EAE, induced by myelin oligodendrocyte glycoprotein (MOG)-specific T cells, the lack of neurological signs was ascribed to a decrease of macrophages and parenchymal inflammation, whereas perivascular inflammation and the synthesis of TNF, IFN-gamma, and interleukin-6 was clearly present. In our system, however, the timely onset of paralysis and the morphologically similar appearance of infiltrates in some of the treated animals argues against such a phenomenon. We propose that during rolipram treatment of clinically manifest EAE, suppression of local TNF production in addition to its other effects is crucial regardless of the discrepancy between the histological and clinical scores. Using in-situ hybridization, it was shown recently that the presence of TNF expressing cells in the CNS correlates well with clinical signs in EAE. Using this approach it should be possible to identify the rolipram-sensitive cell types in EAE and MS lesions—inflammatory cells, glial cells, or both.

There is no sufficient therapy for MS today. Interferon-β is now considered the best treatment available for relapsing-remitting MS, since it lessens the frequency of MS attacks by one-third and is well tolerated. However almost all patients receiving interferon-β eventually had attacks, and favorable effects on disability after 3 years were significant but moderate. In EAE the limited T cell receptor (TCR) repertoire of encephalitogenic cells in susceptible animal strains allowed refined and efficient therapies such as antibodies against TCR Vβ8.2 chains and peptide vaccination with Vβ8.2 variable or junctional region sequences (25). In MS, the autoimmune response is more heterogeneous and at present it is unlikely that highly specific immunotherapies will be applicable to humans, especially when used as monotherapy.

In contrast, rolipram by its many effects is expected to be of great therapeutic use in MS and other patients, especially in appropriate combinations, as shown by these and other experiments and as indicated by the considerations already discussed.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A method of preventing or treating multiple sclerosis comprising administering to a host in need thereof synergistically effective amounts of a PDE IV compound according to formula I:

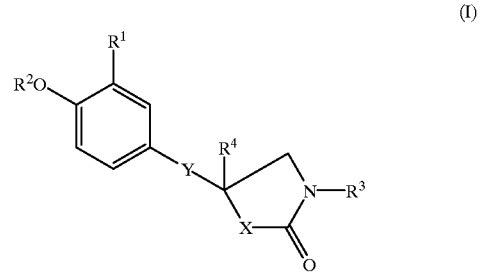

wherein
  $R^1$ is $OR^5$;
  $R^5$ is $C_{1-6}$-alkyl, $C_{3-7}$-cycloalkyl or 3-tetrahydrofuranyl;
  $R^2$ is methyl;
  $R^3$ is a hydrogen atom or $C_{1-6}$-alkanoyl;
  $R^4$ is a hydrogen atom or $C_{1-4}$-alkyl;
  Y is a direct bond;
  X is $CH_2$ group or an oxygen atom; and pharmaceutically acceptable salts thereof; and an interferon.

2. A method according to claim 1, wherein the time between of the severity of symptoms of the episodic recurrences of the multiple sclerosis is ameliorated.

3. A method of claim 1, wherein an inflammatory lesion associated with said multiple sclerosis is prevented or treated.

4. A method according to claim 1, wherein the interferon is interferon-$\beta$.

5. A method of claim 1, wherein the PDE IV inhibitor is rolipram.

6. A method of claim 1, wherein the PDE IV inhibitor is rolipram and the interferon is interferon-beta.

7. A method of preventing or treating multiple sclerosis comprising administering to a host in need thereof synergistically effective amounts of:
- 4-(3-(cyclopentyloxy)-4-methoxyphenyl)-2-pyrrolidinone, or
- 5-methyl-5-(3-propoxy-4-methoxyphenyl)-2-oxazolidinone, or
- pharmaceutically-acceptable salts thereof; and
- interferon.

8. A method of claim 7, wherein the interferon is interferon-$\beta$.

9. A pharmaceutical composition comprising synergistically effective amounts for treating multiple sclerosis of:
- 4-(3-(cyclopentyloxy)-4-methoxyphenyl)-2-pyrrolidinone, or
- 5-methyl-5-(3-propoxy-4-methoxyphenyl)-2-oxazolidinone, or
- pharmaceutically-acceptable salts thereof; and
- interferon.

10. A pharmaceutical composition of claim 9, wherein the interferon is interferon-$\beta$.

11. A pharmaceutical composition comprising synergistically effective amounts for treating multiple sclerosis of:
- 4-(3-(cyclopentyloxy)-4-methoxyphenyl)-2-pyrrolidinone, or
- 5-methyl-5-(3-propoxy-4-methoxyphenyl)-2-oxazolidinone, or
- pharmaceutically-acceptable salts thereof; and
- interferon-$\beta$.

12. A pharmaceutical composition comprising synergistically effective amounts for treating multiple sclerosis of:
- 4-(3-(cyclopentyloxy)-4-methoxyphenyl)-2-pyrrolidinone, or
- 5-methyl-5-(3-propoxy-4-methoxyphenyl)-2-oxazolidinone, or
- pharmaceutically-acceptable salts thereof; and
- interferon.

13. A pharmaceutical composition comprising synergistically effective amounts for treating multiple sclerosis of:
- 4-(3-(cyclopentyloxy)-4-methoxyphenyl)-2-pyrrolidinone, or
- 5-methyl-5-(3-propoxy-4-methoxyphenyl)-2-oxazolidinone, or
- pharmaceutically-acceptable salts thereof; and
- interferon-$\beta$.

14. A method of treating multiple sclerosis comprising administering to a host in need thereof synergistically effective amounts of:
- 4-(3-(cyclopentyloxy)-4-methoxyphenyl)-2-pyrrolidinone, or
- 5-methyl-5-(3-propoxy-4-methoxyphenyl)-2-oxazolidinone, or
- pharmaceutically-acceptable salts thereof; and
- interferon-$\beta$.

15. A pharmaceutical composition comprising synergistically effective amounts of a PDE IV compound according to formula I:

wherein
- $R^1$ is $OR^5$;
- $R^5$ is $C_{1-6}$-alkyl, $C_{3-7}$-cycloalkyl or 3-tetrahydrofuranyl;
- $R^2$ is methyl;
- $R^3$ is a hydrogen atom or $C_{1-6}$-alkanoyl;
- $R^4$ is a hydrogen atom or $C_{1-4}$-alkyl;
- Y is a direct bond;
- X is $CH_2$ group or an oxygen atom; and pharmaceutically acceptable salts thereof; and an interferon.

16. A pharmaceutical composition of claim 15, wherein $R^3$ is hydrogen.

17. A pharmaceutical composition of claim 15, wherein the PDE IV compound is 4-(3-(cyclopentyloxy)-4-methoxyphenyl)-2-pyrrolidinone, or
- 5-methyl-5-(3-propoxy-4-methoxyphenyl)-2-oxazolidinone, or
- pharmaceutically-acceptable salts thereof.

18. A composition of claim 15, wherein the interferon is interferon-$\beta$.

* * * * *